United States Patent
Brauckman et al.

(10) Patent No.: US 6,994,688 B2
(45) Date of Patent: Feb. 7, 2006

(54) CATHETER ATTACHMENT AND CATHETER FOR BRACHYTHERAPY

(75) Inventors: Richard A. Brauckman, Cumming, GA (US); Jack C. White, Alpharetta, GA (US); Glenn A. Dill, Fayetteville, GA (US); Anthony D. Coon, Suwanee, GA (US); Michael R. Moody, Marietta, GA (US)

(73) Assignee: Theragenics Corporation, Buford, GA (US)

( * ) Notice: Subject to any disclaimer, the term of this patent is extended or adjusted under 35 U.S.C. 154(b) by 504 days.

(21) Appl. No.: 09/858,366

(22) Filed: May 16, 2001

(65) Prior Publication Data

US 2001/0056219 A1    Dec. 27, 2001

Related U.S. Application Data

(60) Provisional application No. 60/205,076, filed on May 18, 2000.

(51) Int. Cl.
*A61M 29/00* (2006.01)
(52) U.S. Cl. .............................. 604/103.02
(58) Field of Classification Search ........... 604/96.01, 604/103.02, 103.06, 103.11, 103.13, 264, 604/523, 915, 192, 194, 533; 623/1.11, 1.42; 600/1–8
See application file for complete search history.

(56) References Cited

U.S. PATENT DOCUMENTS

| | | | | |
|---|---|---|---|---|
| 4,546,152 A | * | 10/1985 | Koelmel et al. | 525/437 |
| 4,676,229 A | * | 6/1987 | Krasnicki et al. | 128/4 |
| 4,861,520 A | * | 8/1989 | van't Hooft et al. | 252/644 |
| 5,059,166 A | | 10/1991 | Fischell et al. | |
| 5,084,002 A | | 1/1992 | Liprie | |
| 5,141,487 A | | 8/1992 | Liprie | |
| 5,147,382 A | * | 9/1992 | Gertzman et al. | 606/228 |
| 5,199,939 A | * | 4/1993 | Duke et al. | 600/3 |
| 5,213,561 A | | 5/1993 | Weinstein et al. | |
| 5,282,781 A | * | 2/1994 | Liprie | 600/3 |
| 5,302,168 A | * | 4/1994 | Hess | 600/3 |
| 5,342,283 A | * | 8/1994 | Good | 600/8 |

(Continued)

FOREIGN PATENT DOCUMENTS

DE    19819426    11/1999

(Continued)

*Primary Examiner*—Eduardo C. Robert
*Assistant Examiner*—Anuradha Ramana
(74) *Attorney, Agent, or Firm*—Knoble Yoshida & Dunleavy, LLC

(57) ABSTRACT

A catheter for the positioning of a radioactive material for therapeutic radiation treatment of the body is disclosed. The catheter includes a radioactive source positioned at the distal end thereof and is sufficiently flexible and strong to navigate in the body to the desired treatment location. The radioactive source may be provided to the catheter in a number of different ways. In one set of embodiments, the radioactive source is bonded to the inner or outer surface of the catheter body, a catheter attachment or a carrier positionable within the catheter body. In another set of embodiments, one of the catheter body, catheter attachment or carrier positionable within the catheter body includes a cavity within which the radioactive source is placed. In this set of embodiments, the radioactive source may be provided in a variety of different forms, depending upon the particular needs of the treatment method. The radioactive source may also be immobilized in a polymeric material such as an elastomer, gel, hydrogel, foam or other similar deformable material. Finally, the catheter body or carrier may include a removable portion which provides access to the cavity within which the radioactive source is housed.

34 Claims, 6 Drawing Sheets

U.S. PATENT DOCUMENTS

| | | | | |
|---|---|---|---|---|
| 5,405,309 A | * | 4/1995 | Carden, Jr. | 600/3 |
| 5,498,227 A | * | 3/1996 | Mawad | 600/3 |
| 5,503,614 A | * | 4/1996 | Liprie | 600/7 |
| 5,624,392 A | * | 4/1997 | Saab | 604/43 |
| 5,645,529 A | * | 7/1997 | Fagan et al. | 604/101 |
| 5,683,345 A | | 11/1997 | Waksman et al. | |
| 5,718,684 A | * | 2/1998 | Gupta | 604/96 |
| 5,840,008 A | | 11/1998 | Klein et al. | |
| 5,863,284 A | | 1/1999 | Klien | |
| 5,871,437 A | * | 2/1999 | Alt | 600/3 |
| 5,897,573 A | * | 4/1999 | Rosenthal et al. | 606/224 |
| 5,947,889 A | * | 9/1999 | Hehrlein | 600/3 |
| 6,024,690 A | * | 2/2000 | Lee et al. | 600/3 |
| 6,036,631 A | * | 3/2000 | McGrath et al. | 600/3 |
| 6,042,600 A | * | 3/2000 | Rosenthal et al. | 606/224 |
| 6,175,760 B1 | * | 1/2001 | Baskin et al. | 600/436 |
| 6,183,440 B1 | * | 2/2001 | Bell | 604/110 |
| 6,217,503 B1 | * | 4/2001 | Weinberger et al. | 600/3 |
| 6,231,494 B1 | * | 5/2001 | Verin et al. | 600/1 |
| 6,261,320 B1 | * | 7/2001 | Tam et al. | 623/1.15 |
| 6,352,682 B2 | * | 3/2002 | Leavitt et al. | 424/1.25 |
| 6,428,557 B1 | * | 8/2002 | Hilaire | 606/200 |
| 6,458,069 B1 | * | 10/2002 | Tam et al. | 600/3 |
| 6,508,754 B1 | * | 1/2003 | Liprie et al. | 600/3 |
| 6,569,076 B1 | * | 5/2003 | Larsen et al. | 600/3 |
| 6,589,502 B1 | * | 7/2003 | Coniglione et al. | 424/1.25 |
| 6,749,553 B2 | | 6/2004 | Brauckman et al. | |
| 2002/0019662 A1 | | 2/2002 | Brauckman et al. | |
| 2002/0147379 A1 | | 10/2002 | Moody et al. | |
| 2004/0047444 A1 | | 3/2004 | White et al. | |
| 2004/0138515 A1 | | 7/2004 | White et al. | |

FOREIGN PATENT DOCUMENTS

| | | |
|---|---|---|
| WO | 00/09212 | 2/2000 |

* cited by examiner

CATHETER ATTACHMENT AND CATHETER FOR BRACHYTHERAPY

RELATED APPLICATION DATA

This application claims the benefit of U.S. provisional patent application No. 60/205,076, filed on May 18, 2000, pursuant to 35 U.S.C. §119(e).

FIELD OF THE INVENTION

The present invention relates to apparatus and methods which can be used in brachytherapy to position a radioactive source in the body for delivery of radiation treatment. More particularly, the invention relates to catheters and catheter attachments for positioning a radioactive source to a desired site in the body and methods for treatment of desired locations in the body with radiation which employ such catheters and catheter attachments.

BACKGROUND OF THE INVENTION

The body's healing response to wounds includes the formation of scar tissue. This response occurs in the vascular system after injury or trauma such as may be caused by angioplasty or other similar treatments thereby resulting in a condition commonly referred to as restenosis. As a result of restenosis, scar tissue grows on the inner walls of the vessels vascular system thereby causing an undesirable narrowing of the vessels. Accordingly, it is desirable to prevent or inhibit restenosis as part of the overall treatment of the vascular system following procedures such as angioplasty or the like. While angioplasty currently has a short-term success rate of 90–95%, due to restenosis, about 30–50% of patients' vessels narrow to approximately 50% or less of the size of the native vessel.

A variety of different therapies for the prevention of restenosis have been employed including light therapies, chemotherapeutic agents, stents, atherectomy devices and lasers. One method for preventing or inhibiting restenosis which has shown promise is the irradiation the inner vascular wall subsequent to the treatment in order to prevent or inhibit scar tissue formation, sometimes referred to as intimal hyperplasia. However, the devices for delivery of radiation sources to the treatment site suffer from a number of drawbacks which limit their usefulness and effectiveness.

U.S. Pat. No. 5,084,002 (Liprie) relates to an ultra-thin, high dose iridium source for remote treatment of cancerous tissue with radiation. This device is specifically designed for use in areas of the human body where minimization of trauma to adjacent tissue is a high priority. As a result, the radioactive source is encapsulate in a thin platinum delivery wire with an ultra-thin cross section. A similar device is also disclosed in U.S. Pat. No. 5,141,487 (Liprie).

U.S. Pat. No. 5,302,168 (Hess) relates to a method and apparatus for restenosis treatment after angioplasty by application of a radioactive dose to the reduced region of the artery. In one embodiment disclosed in this patent, a radioactive dose is positioned in a housing at the distal end of a catheter delivery device. The housing is provided with a window cut-out covered by a sheath. The sheath is drawn back when the radioactive dose means is positioned for treatment. A second embodiment disclosed in this patent involves attaching radioactive elements to an angioplasty balloon catheter and expanding the balloon in the area to be treated to force the radioactive elements into contact with the area to be treated.

U.S. Pat. No. 5,213,561 (Weinstein et al.) discloses methods and devices for preventing restenosis after angioplasty. More specifically, various embodiments are disclosed wherein a radioactive source is mounted at the end of a guide wire, is delivered inside a tube provided with a guide wire in a balloon catheter or is coated on a balloon expandable stent. A retractable sheath is employed to enclose the radiation source until irradiation is desired at which point the sheath is retracted.

U.S. Pat. No. 5,199,939 (Dake) discloses a radioactive catheter and a method for using the catheter for preventing restenosis after angioplasty. The method includes employing an elongate, flexible catheter with a radioactive source located in its distal end to irradiate the treatment zone. The radioactive catheter employs a plurality of cylindrical radioactive pellets disposed among a plurality of cylindrical spacers as the radioactive source.

The foregoing embodiments suffer from a number of drawbacks. For example, many of the devices include a number of elements located between the radiation source and the area to be treated which results in shielding which may reduce the effect of the radiation and/or cause an irregular distribution of the radiation dose. Other devices provide the radioactive source material in a plurality of discrete elements which inherently results in different levels of radiation dose being applied to different parts of the treated area. Other drawbacks of specific devices exist as well.

SUMMARY OF THE INVENTION

It is the object of certain embodiments of the present invention to overcome one or more of the drawbacks of existing devices for providing a dose of radiation to a localized treatment area in the body.

It is a further object of certain embodiments of the present invention to provide devices which position the radioactive source in close proximity to the treatment area.

It is a further object of certain embodiments of the present invention to provide devices wherein shielding of the radiation is minimized or substantially eliminated.

It is a still further object of certain embodiments of the present invention to provide devices which deliver a substantially uniform radiation dose to the area to be treated.

These and other objects are accomplished by various embodiments of the present invention which relates, in one aspect, to a catheter for delivery of a radioactive source to a localized area to be treated. The radioactive source may be provided to the catheter in a number of different ways depending upon the particular requirements of a specific treatment method. In embodiments of the invention, the radioactive source may be bonded to the catheter itself, or may be provided in specialized delivery devices housed in or associated with the catheter. As a result of the novel ways of providing the radioactive source to the catheter, a number of the drawbacks of prior art devices can be overcome by devices in accordance with the present invention.

DETAILED DESCRIPTION OF THE PREFERRED EMBODIMENTS

The present invention is directed to a device and method for delivering a radiation source to a desired treatment area in a body. The device and method of the invention may be employed, for example, for preventing stenosis of a vessel in a body by irradiating the vessel and to a variety of different devices for treating vessels with radiation. In addition, the methods and devices of the present invention may also be employed for other treatments such as the repair or correction of the intraluminal lining or iliac or femoral aneurysms; recanalization of injured vessels caused by blunt or penetrating trauma, recanalization of esophageal stenoses associated with carcinoma or benign structures, dilation of the aorta, dilation of biliary stenoses associated with strictures, tumors and cancer of the lungs, bronchial system, colon, brain, pancreas and common bile duct, and treatment of the urethral strictures and tracheal strictures. Other treatments which require irradiation of tissue of the human or mammal body can also be carried out using the various embodiments of the apparatus and methods of the present invention.

The methods and devices of the present invention can be employed to prevent the formation of scar tissue after trauma to the body in particular locations such as that which frequently results after angioplasty. By delivering radioactivity to the portion of the luminal wall soon after the enlargement procedure, excessive growth of scar tissue can be inhibited. As a result, the incidence of repeated angioplastic interventions can be reduced.

Figure 1:
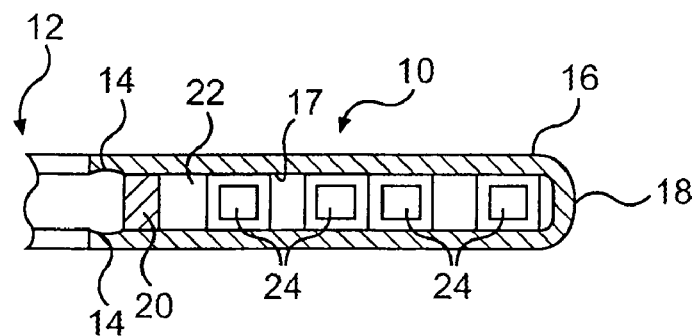
FIG. 1 is a cross-sectional view of one embodiment of a catheter attachment of the present invention.

In a first aspect, the present invention relates to a catheter attachment 10. The catheter attachment 10 is adapted to form the distal end of a catheter 12 such as an intraluminal catheter. As shown in FIG. 1, the catheter attachment 10 may be removably attached to a catheter 12 via any suitable securing mechanism such as a snap fit 14 shown schematically in FIG. 1. Any other suitable conventional attachment means such as a threading means, clips, and an interference fit may be employed to attach catheter attachment 10 to catheter 12. The radioactive source may be chemically or thermally bonded to catheter 12, and catheter 12 may be disposable. Preferably catheter attachment 10 is removably attached to catheter 12 so that it may be removed either prior to a treatment procedure to load the radioactive source material into the catheter attachment 10, and/or after a treatment procedure for, for example, handling and/or for disposal of the radioactive waste material or for other purposes.

In the embodiment shown in FIG. 1, catheter attachment 10 is formed from a suitable catheter material 16 which is deformable and has a rounded end 18 to minimize trauma as the catheter 12 is inserted into the body. Catheter material 16 is preferably a deformable material which can bend so that catheter 12 may be inserted through complicated parts of the body. Catheter 12 may also be inserted within a disposable sheath to avoid direct tissue contamination of the radioactive source. Such disposable catheter sheaths are known to persons skilled in the art and are preferably fabricated from polymeric materials. The cross-section of catheter 12 can be any suitable shape but is most preferably circular since there are then no edges which might cause trauma as the catheter is inserted and removed from the body.

Suitable catheter materials 16 are known in the art. A preferred catheter material 16 is a polyetheramide. Other suitable materials may be employed as long as they are biocompatible, sufficiently flexible to function as a catheter and sufficiently durable so that the catheter material 16 is not breached during normal use.

Also shown in FIG. 1, is a plug 20 which is used to seal the interior cavity 22 of catheter attachment 10 from the rest of catheter 12. Plug 20 is preferably removable from catheter attachment 10 to allow insertion and removal of radioactive source 24 from catheter attachment 10. Radioactive source 24 may be disposed in the interior cavity 22 of catheter attachment 10 in any suitable matter. As shown in FIG. 1, radioactive pellets or seeds can be employed as radioactive source 24, in which case the pellets or seeds are disposed within interior cavity 22 of catheter attachment 10. In one embodiment, radioactive source 24 is of suitable size so that once it is placed within interior cavity 22, it is retained substantially in place by an interference fit with the interior wall 17 of catheter 12, as shown in FIG. 1. Any other suitable way of securing radioactive source 24 in place within catheter attachment 10 may be employed including spacer materials, clips, pockets, chemical or thermal bonding, interference fit, pressure fit or other securing means. In addition, the radioactive source 24 may be secured within catheter attachment 10 in any of the various manners shown in the other figures of this application or described in the specification, even if such figures relate to embodiments of the invention which do not employ a catheter attachment 10.

In a more preferred embodiment, radioactive source 24 is spaced evenly throughout interior cavity 22 over a suitable length for treatment of the entire area of the body which is to be irradiated. The purpose of evenly spacing radioactive source 24 in interior cavity 22 is to provide a substantially uniform radiation distribution about catheter 14 to thereby provide a substantially uniform dose of radiation over the entire treatment zone.

Figure 2:
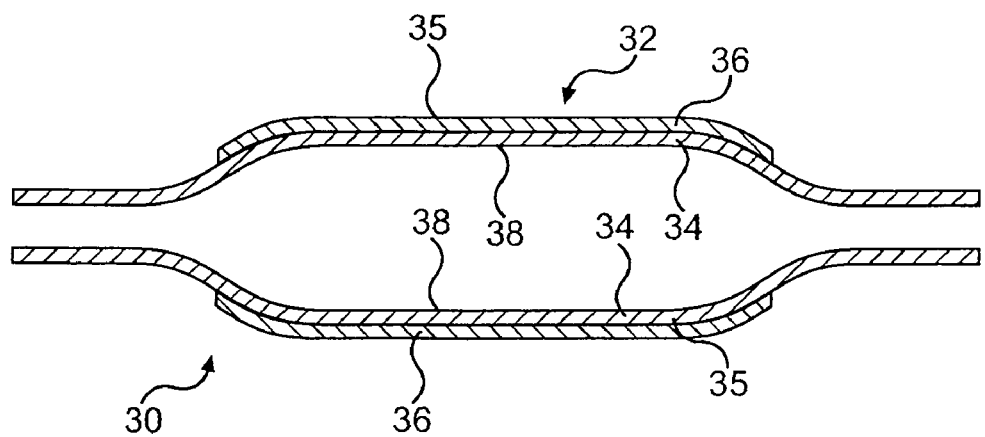
FIG. 2 is a cross-sectional view of a balloon catheter embodiment of the present invention with the radiation source bonded to the outer surface thereof.

FIG. 2 shows an alternative embodiment of the present invention wherein a balloon catheter 30 is employed. Balloon catheter 30 has an expandable portion 32 which is shown in FIG. 2 in the expanded state. Balloon catheters are well known to persons of ordinary skill in the art and conventional balloon catheters are suitable for use with the present invention.

Balloon catheter 30 includes a catheter wall 34 which is expandable in expandable portion 32 and which is made from a flexible, biocompatible material. In the embodiment shown in FIG. 2, radioactive source 36 is bonded to the outer surface 35 of catheter wall 34. Radioactive source 36 is preferably only applied to outer surface 35 of the expandable portion 32 of balloon catheter 30. The expandable portion 32 of balloon catheter 30 may be selected to be of a suitable length for treatment of the area which is to be irradiated.

Upon expansion of expandable portion 32 of balloon catheter 30, radioactive source 36 is positioned closely adjacent to or against the treatment area treatment. In this manner, the effect of the radiation can be maximized since the distance traveled by the radiation to the treatment zone is minimized. In an alternative embodiment, an expandable stent, not shown, may be used in combination with the balloon catheter 30 in which case the expandable stent will be placed around the outside of balloon catheter 30 and expanded to a position against the interior wall of a vessel to support the vessel in an open position. In this embodiment, the radiation source 36 is still positioned relatively close to the vessel wall since only the expandable stent is located between the radiation source 36 and the vessel wall.

Radiation source 36 must be applied in such a manner that upon expansion of the expandable portion 32 of balloon catheter 30 the radiation source 36 does not detach from the outer surface 35 of catheter wall 34. Suitable methods for bonding radioactive source 36 to catheter wall 34 include at least electroless plating, chemical vapor deposition, electroplating, ion implantation, sputtering, physical vapor deposition and the application of a coating of a polymer matrix having radioactive material dispersed therein.

Figure 3:
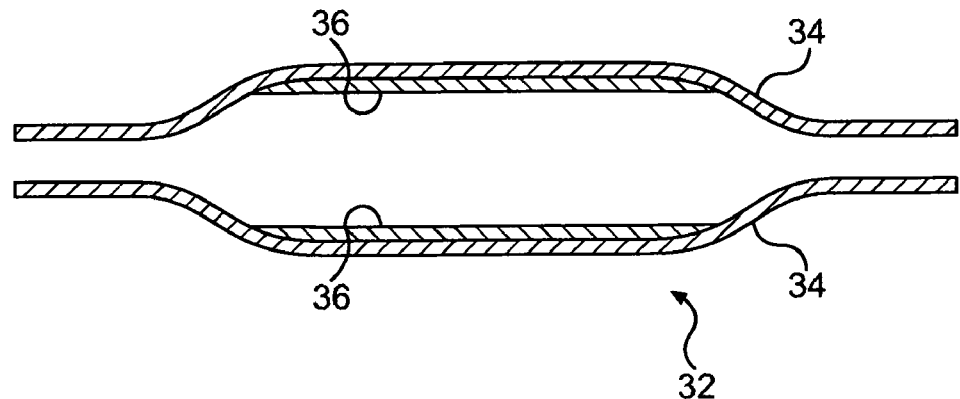
FIG. 3 is a cross-sectional view of an alternative balloon catheter embodiment of the present invention with the radiation source bonded to the inner surface thereof.

As shown in FIG. 3, the radioactive source 36 can alternatively be bonded to the inner surface 38 of catheter wall 34 of balloon catheter 30 in a similar manner as radioactive source is bonded to outer surface 35 of catheter wall 34 in the embodiment depicted in FIG. 2.

In another embodiment similar to that shown in FIGS. 2–3, radioactive source 36 may be dispersed in the expandable portion 32 of catheter wall 34 instead of being bonded to the inner or outer surface of catheter wall 34. In this embodiment, expansion of the expandable portion 32 also brings radioactive source 36 close to the treatment zone. As described below, methods for incorporating radioactive source 36 into a polymeric matrix, for example, may be employed to fabricate this embodiment of the present invention. The radioactive source 36 can be employed as a powder, in solution, in the form of microspheres or pellets or any other suitable form for incorporation into a catheter material.

Figure 7A:
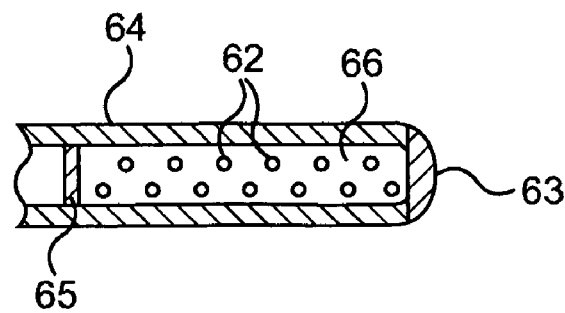
FIG. 7A is yet another embodiment of the present invention wherein the radiation source is embodied in microspheres distributed within the catheter.
Figure 7B:
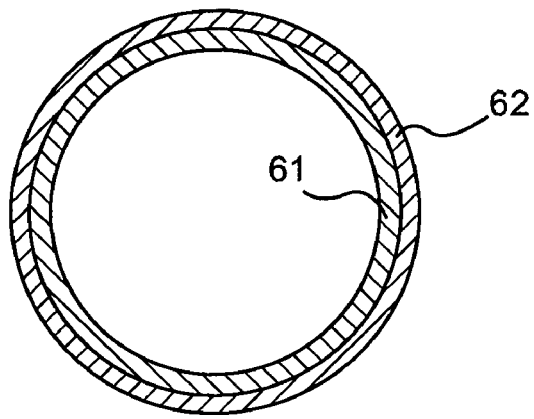
FIG. 7B is a cross-sectional view of one embodiment of a microsphere containing radioactive material in accordance with the present invention.
Figure 7C:
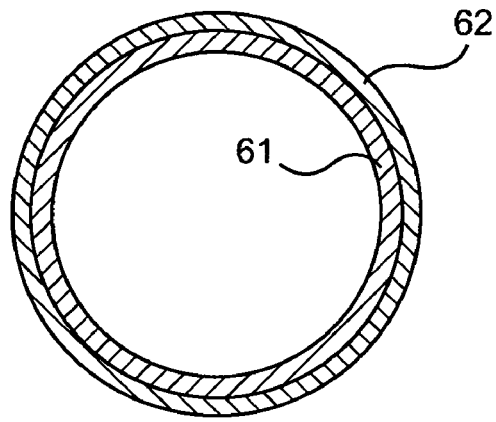
FIG. 7C is a cross-sectional view of a second embodiment of a microsphere containing radioactive material in accordance with the present invention.
Figure 7D:
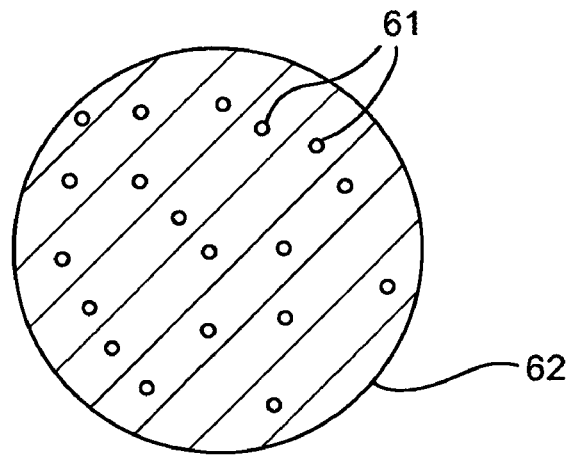
FIG. 7D is a cross-sectional view of a third embodiment of a microsphere containing radioactive material in accordance with the present invention.
Figure 8:
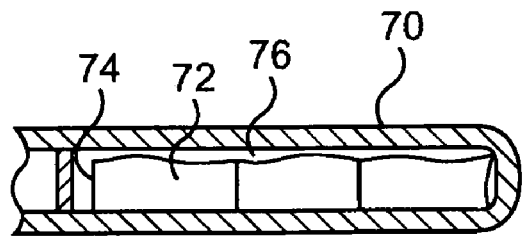
FIG. 8 is a still further embodiment of the present invention wherein the radiation source is embodied in a matrix and included in a catheter.

In addition, embodiments similar to that shown in FIG. 8 may be employed with balloon catheters 30 for delivery of the radioactive source 36. More specifically, the radioactive source 36 can be included in the distal end of an interior housing which may form part of a standard stiffening member which is often employed with such catheters to allow them to be maneuvered through the body. Again, if this type of device is used to deliver the radioactive source 36, any suitable way of associating the radioactive source 36 with the distal end of the stiffening member may be employed, including the ways described in the various embodiments of the present invention shown in FIGS. 1–8 and described in this specification.

Also, the distal end of the stiffening member may be formed as a detachable attachment similar to the catheter attachment 10 described in reference to FIG. 1, except that a variety of different materials could be used to form the stiffening member, in addition to the standard materials used to make catheters. Further, any suitable way of associating the radioactive source 36 with the detachable distal end of the stiffening member may be employed, including the ways described in the various embodiments of the present invention shown in FIGS. 1–8 and described in this specification.

Figure 4:
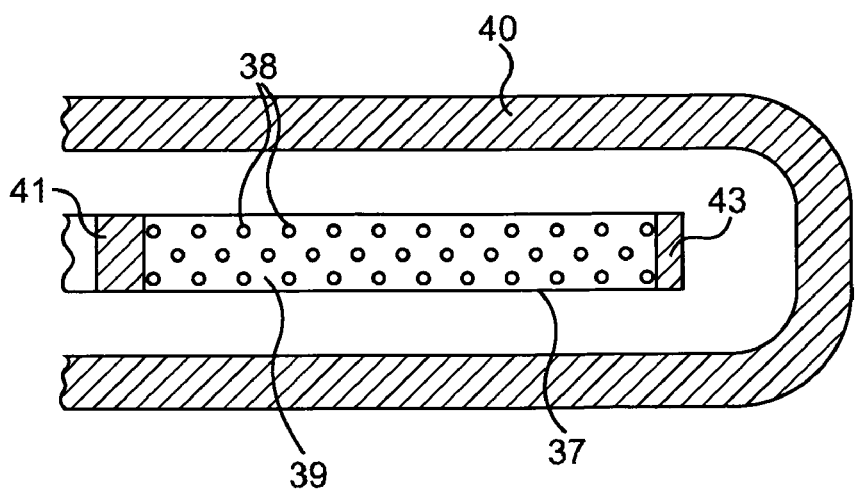
FIG. 4 is a cross-sectional view of an embodiment of a catheter which includes an internal housing within which the radiation source is disposed.

FIG. 4 shows an alternative configuration for the catheter 40 in accordance with the present invention. In this configuration, catheter 40 includes a carrier 37 having a sufficiently small diameter that it can be inserted within the catheter 40. Carrier 37 is preferably sufficiently rigid to promote the insertion and removal of catheter 40 from the body in a conventional manner for such catheters. In this regard, carrier 37 may include stiffening elements, not shown, at various locations along its length in order to provide the requisite stiffness.

Carrier 37 includes the radioactive source 38 in its distal end as shown in FIG. 4. In the embodiment of FIG. 4, the radioactive source 38 can be provided in the form of microspheres as described below. The microspheres 38 may be immobilized in place in carrier 37 by an inert material 39 which is most preferably a material with low shielding properties.

In another embodiment, the radioactive source 38 may be provided in the form of a flexible polymer fiber or strand coated with radioactive material. A polymer is selected as the fiber or strand material which exhibits relatively low radiation shielding and good radiation stability.

Alternative ways of providing the radioactive source 38 to the carrier 37 may be employed. In particular, all of the ways of providing radioactive sources shown in the other figures of the present application, as well as those described in the specification, may be employed to provide the radioactive source 38 to the carrier 37 in embodiments similar to that shown in FIG. 4.

Preferably, the distal end of carrier 37 is closed off from the remainder of carrier 37 by a spacer 41 which may optionally be made from a radioactive shielding material in order to help contain the radioactivity from radioactive source 38 in the treatment area as well as provide visible markers observable using fluoroscopy. In addition, at the very distal end of the carrier 37 may be provided a removable plug 43 which can be employed to access the cavity into which the radioactive source 38 is placed. In use, plug 43 can be removed at the time of use to insert the radioactive source 38 and then be replaced to contain the radioactive source within carrier 37. Plug 43 can also optionally be made from a radioactive shielding material to help contain the radiation from the radiation source 38.

Figure 9:
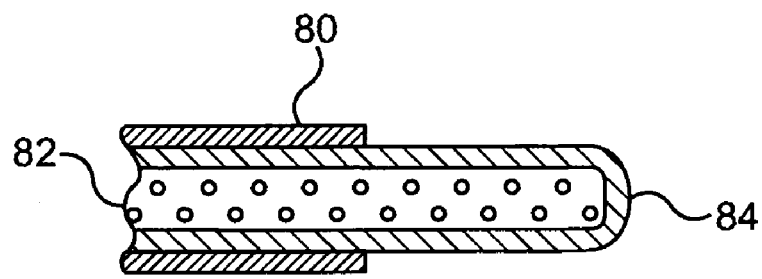
FIG. 9 shows an embodiment of the invention including a retractable sheath.

Optionally, a retractable sheath, shown in FIG. 9, can be associated with carrier 37 in order to provide shielding of the radiation source 38 during insertion and removal of the catheter 40. The details and use of such a retractable sheath are described below with reference to FIG. 9.

Also, the placement of plug 43 at the very distal end of carrier 37 can be adopted for the various other embodiments of the invention described herein. For example, as shown in FIG. 7, a removable plug 63 can be placed at the very distal end of catheter 64 to provide access to the area where the radioactive source 61 is disposed in catheter 64. Such a removable plug may be employed in other embodiments of the invention as well, where the nature of the radioactive source is such that it would be desirable to provide access to the area where the radioactive source is housed for insertion and removal of the radioactive source before and after use.

Figure 5:
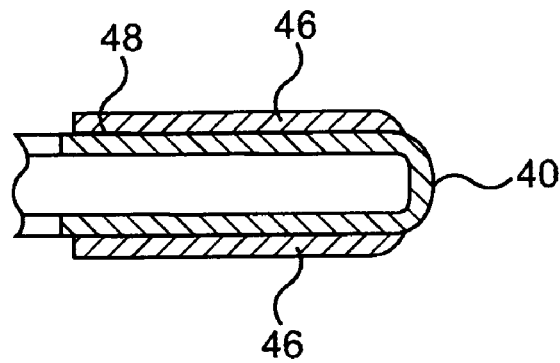
FIG. 5. is a cross-sectional view of another embodiment of the present invention having a radiation source on the outer surface of a catheter.

FIG. 5 shows a similar embodiment to FIG. 2 except with a non-expandable catheter 40. In this embodiment, radioactive source 46 is bonded to the outer surface 48 of catheter 40 in any suitable manner such as those disclosed above with respect to FIG. 2. The FIG. 5 embodiment may also be employed in the form of a catheter attachment as shown in FIG. 1 in which case the radioactive source 46 would be bonded to the outer surface of the catheter attachment.

Figure 6:
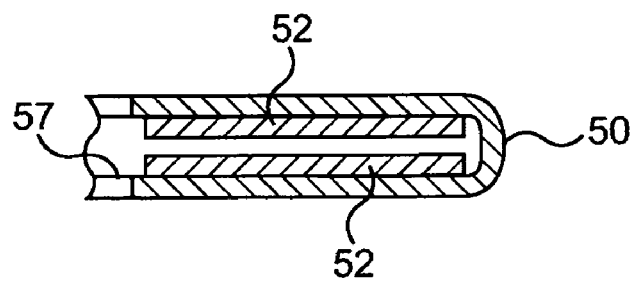
FIG. 6 is a further embodiment of the present invention where the radiation source on an inner surface of a catheter.

Referring now to FIG. 6, there is shown yet another embodiment of the present invention for a non-expandable catheter 50 wherein radioactive source 52 is bonded to the inner surface 54 of catheter 50. The FIG. 5 embodiment may also be employed in the form of a catheter attachment as shown in FIG. 1 in which case the radioactive source 52 would be bonded to the inner surface of the catheter attachment. Also, the embodiments of FIGS. 5–6 can be combined by bonding the radioactive source to both the inner and outer surfaces of the catheter.

FIG. 7A depicts a still further embodiment of the present invention similar to that shown in FIG. 1 except that instead of pellets or seeds of radioactive source materials the embodiment of FIG. 7A employs microspheres 62 which embody the radioactive source 61. As with the catheter embodiments described above, the radioactive source 61 may be bonded to the outer surface of microspheres 62, as shown in FIG. 7B, or, in the case of hollow microspheres 62, the radiation source 61 may be bonded to the inner surface of the hollow microspheres 62, as shown in FIG. 7C. Alternatively, the radioactive source 61 may be dispersed within the material of each microsphere 62 as shown in FIG. 7D, particularly if the microspheres 62 are made from a polymer matrix material.

Microspheres 62 are preferably distributed in catheter 64 in some form of flexible substrate material such as an elastomer, gel, hydrogen, foam or other similar, suitable material 66 to prevent microspheres 62 from migrating from a desired location within the catheter 64, while at the same time maintaining the catheter 64 sufficiently flexible for use. Preferably, the elastomer, gel, hydrogel, foam or other similar material 66 serves to retain microspheres 62 within catheter 64 in a substantially uniform distribution to thereby provide a substantially uniform radiation dose over the entire treatment zone. The radiation source 62 is preferably separated from the remainder of catheter 64 by a spacer 65. Optionally, the catheter 64 of FIG. 7A may be provided with a removable plug 63 at the distal end thereof to provide access to the area where the radioactive source 61 is housed.

Referring now to FIG. 8, there is shown a still further embodiment of the present invention wherein catheter 70 includes radioactive source material 72, shown in powder form, dispersed within a polymeric matrix 74 which is then inserted into cavity 76 of catheter 70. One advantage of this embodiment is that the radioactive material can be fabricated in longer lengths of polymer matrix material and at the time of use be cut to the desired length for the particular treatment zone.

FIG. 9, shows an embodiment of the present invention which includes a retractable sheath 80 which fits over the distal end 82 of catheter 84 in order to shield the radioactive material during insertion, removal and handling of catheter 84. Retractable sheath 80 may be actuated by any suitable means known to those of skill in the art. Retractable sheath 80 may be used with any of the various embodiments of the present invention, including those employing a catheter attachment, those employing a balloon catheter or those employing a catheter with a radioactive source material associated therewith.

In use, the retractable sheath 80 is placed in position over the portion of catheter 84 which contains the radioactive source to shield medical personnel and the patient from radiation during handling and insertion of the catheter 84 to position the radioactive material in the treatment zone. Once the radioactive material is positioned in the treatment zone, the retractable sheath 80 is retracted to expose the radiation source and permit irradiation of the treatment zone. When treatment is completed, the retractable sheath 80 is repositioned over the radioactive source to shield the patient and medical personnel during removal and storage or disposal of the catheter 84.

Figure 10:
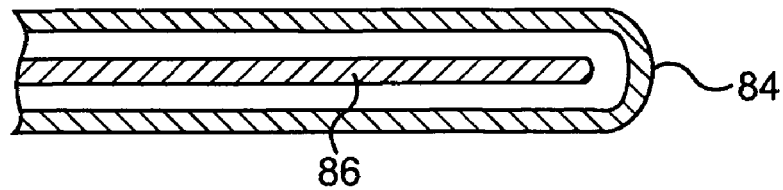
FIG. 10 is an embodiment of the invention employing an isotopically engineered radiation source designed to deliver an appropriate therapeutic radiation dose over a specified time period.

Referring now to FIG. 10, there is a shown an isotopically engineered source 86 designed to deliver an appropriate therapeutic dose of radiation over a predetermined treatment area and treatment time. Source 86 may be engineered to have a specific isotopic composition of materials for the purpose of adjusting the level of activity of the radiation source 86 and, optionally, to reduce trace elements in the radiation source 86 which may produce undesirable radiation. Also, two or more different radioactive isotopes can be engineered into a single source 86, if desired. Radioactive source 86 may be employed with the various catheter devices of the present invention in the form of a wire which may be cut to a suitable length and associated with the catheter as shown in one or more of the above figures.

Preferably, radioactive source 86 is made from isotopes which may be activated in a reactor to provide the desired level of radioactivity for treatment. Such a source 86 can be activated for use and then decayed to a low level of radioactivity for reuse. Source 86 can be reused by reactivating source 86 up to ten times depending on the level of radioactivity required for treatment and the concentration of trace elements in source 86. Alternatively, source 86 can be reused by dissolving and purifying the material and forming a new source 86 from the materials obtained from the purification process. In this manner, maximum use of the expensive isotopes employed as radiation sources can be made.

Figure 13:
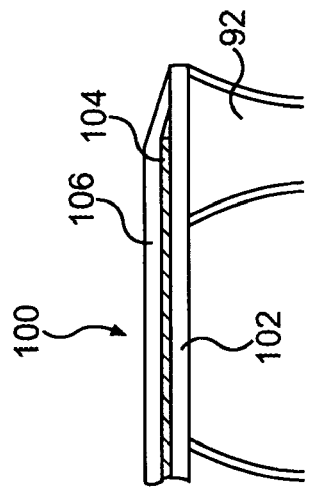
FIG. 13 is an expanded view of the portion of the expandable radiation delivery device indicated in FIG. 11.
Figure 12:
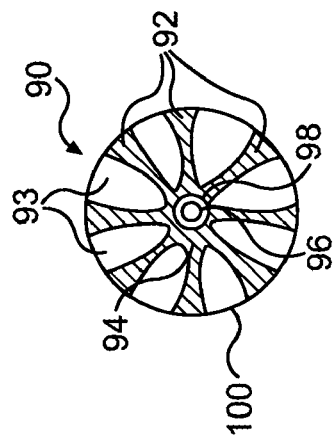
FIG. 12 is a cross-sectional view of the expandable radiation delivery device along line 12—12 in FIG. 11.
Figure 11:
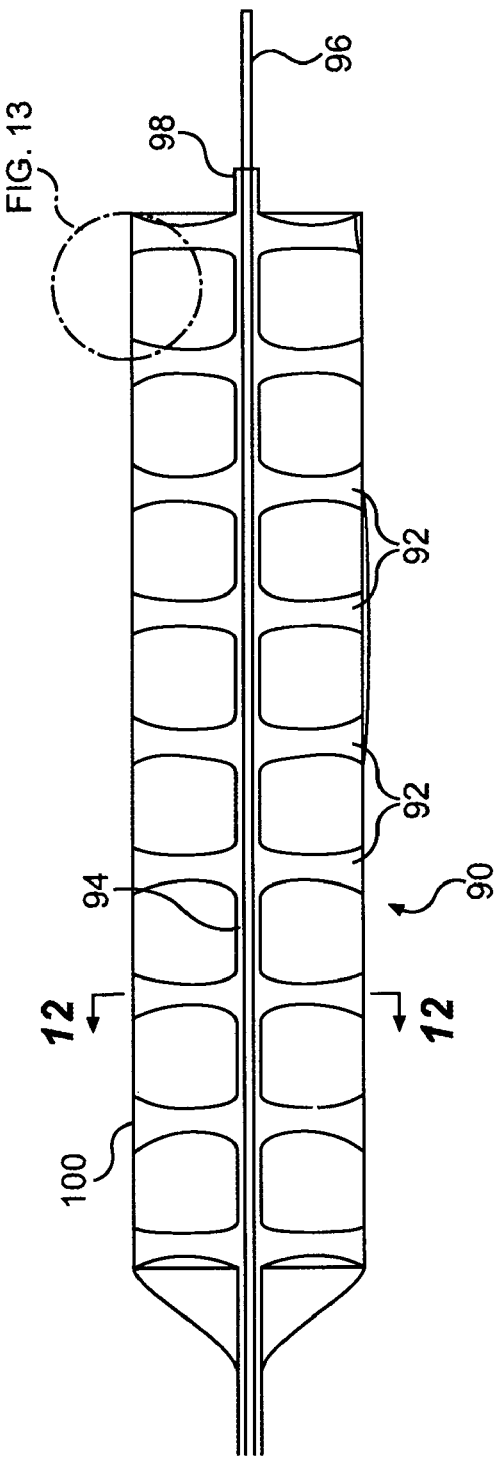
FIG. 11 is a cross-sectional view of an expandable radiation delivery device in accordance with another embodiment of the present invention.

FIGS. 11–13 depict a catheter attachment or catheter device which is expandable to conform to the treatment zone for the purpose of immobilizing the radioactive material in the treatment zone. In use, this device will be positioned in the treatment zone and saline or a comparable material will be forced into the device to radially expand the device toward the boundaries of the treatment zone. Once the radioactive material is in the desired position in the treatment zone and relative to the boundaries of the treatment zone, the expansion is ceased and the radioactive material is permitted to dwell in the treatment zone until the prescribed dose has been delivered.

Once treatment is completed, the device may be removed by withdrawing the saline or other comparable material to thereby collapse the device. The collapsed device may then be removed from the treatment zone using the delivery catheter which was employed to originally position the device in the treatment zone.

A device which may be employed in this way is shown in FIGS. 11–13. More particularly, FIG. 11 shows a cross-sectional side view of a device 90 suitable for use with a catheter, as part of a catheter or as a catheter attachment. Device 90 may include chambers 92 interspersed throughout device 90 which chambers 92 are in fluid communication with a fluid pathway 94. Chambers 92 are spaced such that their remain pathways 93 through which bodily fluids such as blood may flow during use of the device 90 to deliver a radiation dose to a treatment zone.

The device 90 may be mounted on a guide wire 96 such as that used for directing a catheter through a body. Guide wire 96 is preferably enclosed in a tubular channel 98 through the center of device 90 to retain device 90 in a fixed position relative to guide wire 96.

The outer housing 100 of device 90 is formed from an expandable elastic material which encloses the entire device 90 as shown in FIGS. 11–13. Housing 100 preferably includes an inner elastic layer 102, a radioactive source 104 and an outer coating 106 as shown in FIG. 13. Inner elastic layer 102 forms the wall of the chambers 92 to enclose saline solution, gel, foam or other comparable materials used to expand device 90 therein. Radioactive source 104 includes one or more radiation sources. The radiation source may be coated onto the inner elastic layer 102 as shown in FIG. 13 or it may be impregnated or implanted into inner elastic layer 102, as desired and in any suitable manner such as the processes disclosed herein. Outer coating 106 may be employed to isolate the radioactive source layer 104 from direct contact with the body and is preferably made from a biocompatible material which is radiation stable. Inner elastic layer 102 is also preferably formed from a radiation stable materials such as an elastomer.

In use, device 90 can be expanded in the treatment zone to immobilize the radiation source in the treatment zone for the duration of the treatment. Device 90 has the further advantage that it places the radioactive source 104 in close proximity to the tissue to be treated by virtue of expansion of the device 90 thereby maximizing the therapeutic effect of the radiation dose. Another advantage of device 90 is that due to the design and location of the chambers 92, there remain open pathways through the device 90 such that the device will not occlude an artery or vein, for example, during treatment. Finally, since device 90 is specially designed to conform to a particular body cavity when expanded, the treatment minimizes trauma to the treatment zone since the device 90 will not exert undue pressure on tissue in the treatment zone since it merely conforms to the body and does not substantially deform the body tissue in use as would a stent, for example.

The device 90 may be made from a absorbable material so that device 90 can be permanently implanted into the body, if desired. Alternative, device 90 may be disposable such that it can be thrown away after each use and replaced by a new, sterile device. This is particularly advantageous in the embodiment where device 90 is a catheter attachment. Device 90 is particularly suitable for use in treatment of restenosis though it may be used to treat any area of the body and it may be customized to conform to the shape of any body parts or body cavities. The radiation source 104 may preferably be provided to the device 90 in any of the manners described above with respect to the balloon catheter embodiments of the invention, as well as in any other suitable manner described herein.

The radiation source may be any suitable radioactive material known for use in therapeutic treatment of the human or animal body. Preferred radioactive sources are gamma and/or beta-emitting sources. Examples of suitable radioactive sources are Iodine-125, palladium-103, strontium-90, ruthenium-106, phosphorus-32, samarium-145, iridium-192, cobalt-60, radioactive vanadium-48 and yttrium-90. The radioactive source may be selected based on the specific needs of the particular treatment process, the half-life, the amount of radiation required and other parameters.

The radiation source preferably comprises palladium-103 ("Pd-103"), and more preferably comprises carrier-free Pd-103, although even in preferred embodiments, mixtures of carrier-free Pd-103 and reactor grade Pd-103 may also be employed in some applications. Reactor grade Pd-103 may also be employed without carrier-free palladium-103 in some applications.

Reactor grade Pd-103 may be prepared in any suitable conventional manner such as by activation of palladium metal or by fabrication in a nuclear reactor. One disadvantage of reactor grade Pd-103 is that it may contain other undesirable radioactive palladium isotopes such as Pd-109 which emit potentially harmful types of radiation. Reactor grade Pd-103 can be fabricated to minimize such impurities. Nevertheless, in some applications, particularly those where irradiation will occur close to a vital internal organ, it may be desirable to avoid use of reactor grade Pd-103 for this reason. Moreover, the activity of reactor grade Pd-103 is relatively low.

Carrier-free Pd-103, on the other hand, can be made as a highly pure material which contains essentially no undesirable radioactive isotopes of palladium. Moreover, carrier-free Pd-103 can be made having extremely high activities relative to reactor grade Pd-103 thereby providing greater flexibility in adjusting the specific activity of the radiation delivery device and permitting the use of smaller quantities of the expensive palladium material to achieve the same level of radiation dose. In accordance with the present invention, carrier-free Pd-103 can preferably be prepared in a particle accelerator.

In a preferred embodiment, the radiation source material further comprises a diluent. The diluent can be added to the radiation source material after it is eluted off the final purification anion exchange column. Alternatively, the diluent can be added during or prior to a purification process, if the diluent properties so allow. Suitable diluents for radioactive sources may include platinum metal, palladium metal, rhodium metal, one or more of the various substrate materials listed above, or any other suitable material which is compatible with the radiation released by the radioactive source. More preferred diluents are biocompatible materials. Preferred diluents for carrier-free palladium are rhodium and palladium metals, usually in the form of a soluble metal salt such as $PdCl_2$. Because palladium metal will have the same affinity for an anion exchange column as the Pd-103, it can be added as a diluent prior to a purification step employing an anion exchange column and can be co-purified along with the radioactive Pd-103.

Other preferred diluents for the various radioactive sources are certain polymeric materials which can be employed by, for example, homogeneously mixing the radiation source material with the polymer prior to its application to the substrate, or even by carrying out such mixing and using the mixture of polymeric material and radiation source material as the substrate itself.

Although the diluent may normally be considered an undesirable additive in a low energy emitting radiation source due to self-shielding effects, its addition in accordance with the present invention has been found to be advantageous in several respects which, in some applications, may make use of such a diluent desirable. Foremost, the added diluent can serve to promote strong adhesion of the radiation source material to the substrate, thereby forming a physiologically inert layer which will not allow the radioactive source to be mobilized into the circulation of a patient being treated.

Secondly, the addition of diluent provides the ability to adjust the specific activity of the radiation delivery device. This adjustment can be employed to provide an accurately determined desired level of therapeutic or apparent activity, as well as to compensate for the self-shielding effects of the diluent. Thirdly, if purification of the radioactive source is necessary, the presence of the diluent can, in some instances, reduce the loss of radioactive source occurring during the purification process.

The amount of diluent added, therefore, will vary depending principally upon the amount of radioactive source material. Preferably, from about 0.01 mg. to about 500 mg. of diluent per mCi of radioactive source material area can be used. Such amounts of diluent can ensure uniformity of the radioactive source in the radiation delivery device and can promote adherence of the radiation source material to the substrate.

If design considerations, e.g., the desired mass or therapeutic activity of the delivery device, so allow, nuclear reactor produced radioactive source material can be added as a diluent to carrier-free radioactive source material and vice versa. Such addition may be employed, for example, to adjust the therapeutic activity of the radiation delivery device or to reduce the overall cost.

In one embodiment, the substrate can be formed from a non-toxic metallic, non-metallic, polymeric, or ceramic material. The substrate can be in the form of a microsphere, pellet, fiber, ribbon, mesh, patch, film, suture, staple, clip, pin, a hollow tube, or the like. Further, the substrate can be rigid, deformable, solid, hollow, porous, or even sufficiently porous to allow for tissue growth therein.

The substrate can be a non-metallic or low density metallic pellet or microsphere formed from, for instance, aluminum, carbon, diamond, or graphite. The pellets or microspheres can be of any desired shape, but are preferably cylindrical. Of these substrates, graphite in the form of cylindrical pellets or microspheres is particularly preferred.

In another embodiment, the substrate can be a thin film, fiber, ribbon, mesh, patch, suture, or the like formed from a biocompatible polymeric material. The polymeric material is preferably be selected from the group consisting of polyvinyl chloride, polysulfones, polyurethanes, polyamides, polyolefins, polyimides, cellulose esters, nylon, polyesters and modified or derivatized versions of one or more of these polymers. The skilled person is aware of the types of polymeric materials which are biocompatible and radiation stable which can be employed herein. Radiation can cause degradation of certain polymeric materials, as is known in the art. Particularly preferred polymeric materials for forming the substrate are polymeric materials which are resistant to such degradation due to exposure to radiation, such as the radiation stabilized polypropylene materials disclosed in U.S. Pat. Nos. 5,122,593 and 5,140,073, the disclosures of which patents are hereby incorporated by reference to the extent that they relate to radiation stabilized polymeric materials suitable for use as substrates in the present invention.

Optionally, the polymeric materials forming the substrate can include one or more additives to enhance the adherence of the radiation source material to the substrate. Examples of such additives include absorbent materials such as activated carbon powder, activated charcoal, and ion exchange resins. Suitable ion exchange resins include sulfonated polystyrene resins, methylene-sulfonic phenolic resins, phosphoric polystyrene resins, polystyrene resins containing quaternary ammonium groups, pyridinium polystyrene resins, epoxy-polyamine resins containing tertiary and quaternary ammonium groups, iminodiacetic polystyrene resins, acrylic resins and polystyrene resins containing polyamine groups. Skilled persons are familiar with other additives which may be employed in the polymeric substrate for various reasons or specific applications.

In yet another embodiment, the substrate can be formed from a biodegradable polymeric material such as polyethylene glycol or polyethylene glycol-polyethylene oxide block copolymer. Further, the substrate can be formulated as a hydrogel of any of the above mentioned polymeric materials. A particularly preferred substrate is made from a deformable material such as an elastomer, a gel a hydrogel, a foam or other similar, suitable, deformable polymer material such as urethanes, silicones and elastomers, gels or foams based on the above.

In another embodiment, the substrate includes a coating on the surface thereof which promotes one or more of electroplating, chemical vapor deposition or electroless plating. In this manner, a relatively inexpensive substrate can be employed to provide the bulk of the substrate material and, at the same time, good adhesion of the radioactive source to the substrate can be obtained by applying a suitable coating onto which the radioactive source can be bonded via one or more processes such as electroplating, chemical vapor deposition and electroless plating. Suitable coating materials for promoting electroplating, chemical vapor deposition or electroless plating onto a substrate are known to those of skill in the relevant art.

As mentioned previously, the radiation source material can be applied to the outer surface of the substrate or be incorporated into the substrate. Particularly preferred methods for applying the radiation source material onto the surface of the substrate include electroless plating, chemical vapor deposition ("CVD"), physical vapor deposition, ion implantation and sputtering. In some embodiments it may also be desirable to apply the radiation source material to electroconductive substrates via electroplating.

Electroless plating of radioactive source material onto a substrate has the advantage that it the process is applicable to a wide variety of substrates including non-conductive substrates. The process of the invention involves a first step cleaning the substrate surface to which the plating will be applied. Conventional cleaning processes can be employed such as ultrasound, rinsing with solvents and/or water, and other known surface cleaning processes. Once cleaned, the surface of the substrate is pretreated with, for example, $SnCl_2$ or $PdCl_2$. The stannous ions on the surface which result from this pretreatment process serve to attract palladium ions.

For electroless plating of Pd-102 (a precursor for making radioactive Pd-103 in situ) or Pd-103, the pretreated substrate is then activated with, for example, a $PdCl_2$/HCl solution. The stannous ions cause the $Pd_{2+}$ ions from $PdCl_2$ to reduce to $Pd^0$ and to adhere to the substrate. These $Pd^0$ sites form a catalytic surface on the substrate to enhance the deposition of Pd-102 or radioactive Pd-103 onto the substrate in a subsequent plating step. Other, similar metals, such as platinum group metals, may also be used in this step instead of palladium.

The Pd-102 or radioactive Pd-103 can then be deposited on the activated substrate by submerging the substrate in a heated solution of enriched Pd-102 or radioactive Pd-103. Once the deposition reaction subsides, the substrate plated with Pd-102 or radioactive Pd-103 is then dried and cooled. The electroless plating process has the additional advantages that there is very little loss of expensive palladium during the process and that a substantially uniform coating can be applied to a substrate in a relatively short time period. Also, the electroless plating process can be employed to provide a conductive coating on a non-conductive substrate to prepare the substrate for subsequent electroplating of the radioactive materials thereon.

Processes for electroplating Pd-103 onto various electroconductive substrates are known to persons skilled in the art from U.S. Pat. No. 5,405,309, the disclosure of which is incorporated by reference for the purpose of describing the details of a suitable electroplating process for Pd-103. For other radioactive source materials, similar electroplating processes can be used. Also, in many cases if there is sufficient mass of the radioactive source material available, conventional electroplating processes may be suitable for application of the radioactive source to the substrate.

Alternatively, the radiation source material can be uniformly mixed with a diluent and then coated onto the outer surface of the substrate. Preferably, the radiation source material is dissolved in the diluent although it may also be in the form of a particle suspension, if desired. Suitable diluents for this purpose include those described above as well as the substrate materials described above which may be used in polymer masterbatching processes, for example. Preferred diluents are adhesives and polymeric materials such as, for example, urethanes, acrylics, chloroprenes, polyvinyl alcohols, polyvinyl chlorides, nylons, or the like.

In embodiments where the radiation source material is incorporated directly into the substrate, this can be accomplished, for example, using ion implantation or by physically mixing the radiation source material with the substrate material and then forming the substrate from the mixture. For instance, the radiation source material can be uniformly mixed with a polymer powder starting material and be incorporated into the polymer matrix upon polymerization to form the substrate. Such a process is also applicable and particularly preferred when employing elastomeric, gels, hydrogel, foams or other similar substrates. In a more preferred process, the radiation source material is mixed with a polymeric material and subsequently coated, plated or otherwise adhered to the outer surface of the substrate to form an outer, radioactive layer. This delivery device has the advantages that the radiation source material is firmly held in place in the polymer matrix, while at the same time the bulk of the radiation source material is located close to the surface of the substrate to thereby minimize self-shielding effects.

In certain preferred embodiments of the present invention, the radiation source material may be applied to the outer surface of a polymer pellets, microspheres, powders or other similar materials and then the solid polymers containing radioactive source material are physically mixed with a substrate material as described above. These embodiments are similar to polymer masterbatching techniques known to skilled persons for the purpose of incorporating various additives into polymeric materials.

The radiation source material can be supplied to above-described incorporation processes as a solid or in solution, as may be appropriate for the particular incorporation process. If supplied as a solid, the radiation source material can be a powder, or a mixture of radioactive source material and a suitable solid diluent. Alternatively, the radiation source material may be supplied as solid reactor grade radioactive source material or as a solid form of a precursor of the radioactive source which may later be activated in situ, after application of the precursor to the substrate of the radiation delivery device.

If supplied as a solution, the radiation source material can be, for example, a palladium amine complex obtained directly from a purification process. Alternatively, the radioactive source can be dissolved in an appropriate solvent to obtain a desired solution for a particular incorporation process. Suitable solvents for these materials are known in the art.

The foregoing embodiments of the invention have been presented for the purpose of illustration and description only and are not to be construed as limiting the scope of the invention in any way. The scope of the invention is to be determined from the claims appended hereto.

What is claimed is:

1. A catheter useful for radiation treatment of a body which comprises:
    an elongate, flexible catheter body having a proximal section and a distal section;
    a radioactive source housed within a cavity in the distal section of the catheter body, the radioactive source providing radiation in an amount of from about 0.5 microcuries to about 300 curies per centimeter length of the radioactive portion of the catheter body;
    at least a portion of the catheter body being removable to provide access to the cavity wherein the radioactive source is housed, and wherein the removable portion of the catheter body is a catheter attachment which encloses the cavity within which the radioactive source is housed, and the catheter attachment includes a plug which may be removed to provide access to the interior of said cavity; and
    wherein the catheter body is sized and has sufficient strength and flexibility to navigate a portion of a body so that the radioactive source can be positioned at a desired location for treatment.

2. A catheter as claimed in claim 1, wherein the radioactive source is provided in a form selected from the group consisting of: microspheres, pellets, fiber, ribbon, mesh, patch and film.

3. A catheter as claimed in claim 1, wherein the radioactive source is immobilized in a polymeric material.

4. A catheter as claimed in claim 3, wherein the polymeric material is a flexible polymeric material selected from the group consisting of elastomers, gels, hydrogels and foams.

5. A catheter as claimed in claim 4, wherein the polymeric material is selected from the group consisting of: polyimides, polyolefins, and polyesters.

6. A catheter as claimed in claim 1, further comprising a retractable sheath which comprises a radiation shielding material, said retractable sheath being positionable in a first, shielding position, wherein the sheath encloses the portion of the catheter body in which the radioactive source is housed, and a second, retracted position which exposes the portion of the catheter body in which the radioactive source is housed to permit radiation treatment of a desired location in the body.

7. A catheter as claimed in claim 1, wherein the radioactive source comprises carrier-free palladium-103.

8. A catheter useful for radiation treatment of a body which comprises:
   an elongate flexible catheter body;
   an elongate, flexible carrier having a proximal section and a distal section;
   a retractable sheath which comprises a radiation shielding material, said sheath being positionable in a first, shielding position wherein the sheath encloses the portion of the flexible carrier and a second, retractable position which exposes the portion of the flexible carrier in which the radioactive source is housed to permit radiation treatment of a desired location in the body;
   a radioactive source housed within a cavity in the distal section of the flexible carrier, the radioactive source providing radiation in an amount of from about 0.5 microcuries to about 300 curies per centimeter length of the radioactive portion of the flexible carrier;
   at least a portion of the flexible carrier being removable to provide access to the cavity wherein the radioactive source is housed; and
   wherein the flexible carrier is sized and has sufficient strength and flexibility to navigate a portion of the body so that the radioactive source can be positioned at a desired location for treatment.

9. A catheter as claimed in claim 8, wherein the radioactive source is provided in a form selected from the group consisting of: microspheres, pellets, fiber, ribbon, mesh, patch and film.

10. A catheter as claimed in claim 8, wherein the radioactive source is immobilized in a polymeric material.

11. A catheter as claimed in claim 10, wherein the polymeric material is a flexible polymeric material selected from the group consisting of: elastomers, gels, hydrogels and foams.

12. A catheter as claimed in claim 11, wherein the polymeric material is selected from the group consisting of: polyimides, polyolefins, and polyesters.

13. A catheter as claimed in claim 8, wherein the radioactive source comprises carrier-free palladium-103.

14. A catheter attachment useful for radiation treatment of a body which comprises:
   a substrate;
   a radioactive source associated with the substrate, said radioactive source and substrate being positioned within a portion of the catheter attachment, the radioactive source providing radiation in an amount of from 0.5 microcuries to about 300 curies per centimeter length of the portion of the catheter attachment in which said radioactive source is positioned; and
   attachment means for releasably attaching the catheter attachment to the catheter at or near the distal end of the catheter so that the catheter can be employed to position the radioactive source at a desired location for treatment.

15. A catheter attachment as claimed in claim 14, wherein the radioactive source is bonded to a surface of the substrate of the catheter attachment with sufficient bond strength that under normal conditions of use of the catheter attachment, the radioactive source will not detach from the catheter attachment.

16. A catheter attachment as claimed in claim 15, wherein the radioactive source is bonded to an external surface of the catheter attachment.

17. A catheter attachment as claimed in claim 15, wherein the radioactive source is bonded to an internal surface of the catheter attachment.

18. A catheter attachment as claimed in claim 14, wherein the catheter attachment includes an expandable portion and the radioactive source is bonded to the surface of the expandable portion.

19. A catheter attachment as claimed in claim 14, wherein the substrate defines a housing and the radioactive source is housed in the housing.

20. A catheter attachment as claimed in claim 19, wherein the radioactive source is housed in the housing and is provided in a form selected from the group consisting of: microspheres, pellets, fiber, ribbon, mesh, patch and film.

21. A catheter attachment as claimed in claim 19, wherein the radioactive source is immobilized in a polymeric material.

22. A catheter attachment as claimed in claim 21, wherein the polymeric material is a flexible polymeric material selected from the group consisting of: elastomers, gels, hydrogels and foams.

23. A catheter attachment as claimed in claim 22, wherein the polymeric material is selected from the group consisting of: polyimides, polyolefins, and polyesters.

24. A catheter attachment as claimed in claim 14, wherein the radioactive source comprises carrier-free palladium-103.

25. A device for use with a catheter for delivery of a therapeutic radiation dose to a treatment zone which comprises:
   an expandable housing,
   a plurality of chambers in said housing in fluid communication with a single fluid pathway for introduction and removal of fluid from said plurality of chambers, said chambers and housing being arranged such that upon expansion of the device, a pathway for flow of bodily fluids through said device is provided such that the device does not occlude a vessel or lumen when expanded in said vessel or lumen,
   a mount for mounting the device on a guide wire in a manner whereby the device can be guided through a body using said guide wire, and
   a radiation source associated with said device,
   a radiation stable outer coating which isolates the radioactive material from direct contact with the body to be treated during use of the device;
   said device being sized such that when expanded, the device conforms to the treatment zone to thereby substantially immobilize the device in the treatment zone.

26. The device as claimed in claim 25, wherein the radiation source is located on or substantially adjacent to an outer surface of the housing.

27. A device as claimed in claim 26, wherein the device comprises a polymeric material selected from the group consisting of: polyimides, polyolefins, and polyesters.

28. The device as claimed in claim 25, wherein the device is sized such that when expanded it conforms to the size of the treatment zone without substantially deforming surrounding body tissue to thereby minimize trauma in the treatment zone.

29. A catheter useful for radiation treatment of a body which comprises:
   an elongate, flexible catheter body having a proximal section and a distal section;
   a radioactive source housed within a cavity in the distal section of the catheter body, the radioactive source providing radiation in an amount of from about 0.5 microcuries to about 300 curies per centimeter length of the radioactive portion of the catheter body;

at least a portion of the catheter body being removable to provide access to the cavity wherein the radioactive source is housed;

a retractable sheath which comprises a radiation shielding material, said retractable sheath being positionable in a first, shielding position, wherein the sheath encloses the portion of the catheter body in which the radioactive source is housed, and a second, retracted position which exposes the portion of the catheter body in which the radioactive source is housed to permit radiation treatment of a desired location in the body; and wherein the catheter body is sized and has sufficient strength and flexibility to navigate a portion of a body so that the radioactive source can be positioned at a desired location for treatment.

30. A catheter as claimed in claim 29, wherein the radioactive source is provided in a form selected from the group consisting of: microspheres, pellets, fiber, ribbon, mesh, patch and film.

31. A catheter as claimed in claim 29, wherein the radioactive source is immobilized in a polymeric material.

32. A catheter as claimed in claim 31, wherein the polymeric material is a flexible polymeric material selected from the group consisting of elastomers, gels, hydrogels and foams.

33. A catheter as claimed in claim 32, wherein the polymeric material is selected from the group consisting of: polyimides, polyolefins, and polyesters.

34. A catheter as claimed in claim 29, wherein the radioactive source comprises carrier-free palladium-103.

* * * * *